US010172676B2

(12) United States Patent
Ecabert et al.

(10) Patent No.: US 10,172,676 B2
(45) Date of Patent: Jan. 8, 2019

(54) DEVICE AND METHOD FOR THE COMPUTER-ASSISTED SIMULATION OF SURGICAL INTERVENTIONS

(71) Applicant: Siemens Healthcare GmbH, Erlangen (DE)

(72) Inventors: Olivier Ecabert, Ebermannstadt (DE); Klaus Engel, Nürnberg (DE); Tommaso Mansi, Plainsboro, NJ (US); Ingmar Voigt, Erlangen (DE)

(73) Assignee: SIEMENS HEALTHCARE GMBH (DE)

( * ) Notice: Subject to any disclaimer, the term of this patent is extended or adjusted under 35 U.S.C. 154(b) by 269 days.

(21) Appl. No.: 15/150,607

(22) Filed: May 10, 2016

(65) Prior Publication Data

US 2016/0331464 A1 Nov. 17, 2016

(30) Foreign Application Priority Data

May 12, 2015 (DE) .......................... 10 2015 208 804

(51) Int. Cl.
*A61B 5/055* (2006.01)
*A61B 34/10* (2016.01)
(Continued)

(52) U.S. Cl.
CPC ............ *A61B 34/10* (2016.02); *A61B 5/1128* (2013.01); *A61B 90/37* (2016.02); *G06F 3/016* (2013.01); *G06F 3/017* (2013.01); *G06F 3/0304* (2013.01); *G06F 19/00* (2013.01); *G06K 9/00355* (2013.01); *G06K 9/00671* (2013.01); *G16H 50/50* (2018.01); *A61B 5/0037* (2013.01); *A61B 5/0044* (2013.01); *A61B 5/0073* (2013.01);
(Continued)

(58) Field of Classification Search
CPC ....... A61B 34/10; A61B 5/1128; A61B 90/37; A61B 2034/2065; A61B 5/0044; G16H 50/50; G06K 9/00671; G06K 9/00355; G06F 3/016; G06F 3/0304; G06F 3/017
See application file for complete search history.

(56) References Cited

U.S. PATENT DOCUMENTS

2004/0009459 A1* 1/2004 Anderson ........... G06F 19/3481
434/262
2010/0167253 A1 7/2010 Ryan et al.
(Continued)

*Primary Examiner* — Kyoung Lee
(74) *Attorney, Agent, or Firm* — Schmeiser, Olsen, & Watts LLP

(57) ABSTRACT

A first interface for reading image data of an anatomical region obtained by means of a medical imaging method is provided. A modeling module serves for establishing a volumetric biomechanical structure model of the anatomical region on the basis of the image data. Moreover, provision is made of a tracking module, couplable with a camera, for video-based registration of spatial gestures of a user. Furthermore, a simulation module, based on the biomechanical structure model, serves to assign a registered gesture to a simulated mechanical effect on the anatomical region, simulate a mechanical reaction of the anatomical region to the simulated mechanical effect, and modify the biomechanical structure model in accordance with the simulated mechanical reaction. Moreover, provision is made for a visualization module for the volumetric visualization of the biomechanical structure model.

14 Claims, 2 Drawing Sheets

(51) Int. Cl.
*A61B 90/00* (2016.01)
*G06F 3/01* (2006.01)
*G06F 3/03* (2006.01)
*G06K 9/00* (2006.01)
*A61B 5/11* (2006.01)
*G16H 50/50* (2018.01)
*G06F 19/00* (2018.01)
*A61B 34/00* (2016.01)
*A61B 17/00* (2006.01)
*A61B 34/20* (2016.01)
*G06K 9/62* (2006.01)
*A61B 5/00* (2006.01)

(52) U.S. Cl.
CPC ............... *A61B 5/055* (2013.01); *A61B 34/76* (2016.02); *A61B 2017/00207* (2013.01); *A61B 2034/104* (2016.02); *A61B 2034/105* (2016.02); *A61B 2034/2057* (2016.02); *A61B 2034/2065* (2016.02); *A61B 2090/365* (2016.02); *A61B 2576/00* (2013.01); *G06K 9/627* (2013.01); *G06K 9/6257* (2013.01); *G06K 2209/05* (2013.01)

(56) References Cited

U.S. PATENT DOCUMENTS

| | | |
|---|---|---|
| 2010/0240996 A1 | 9/2010 | Ionasec et al. |
| 2011/0046935 A1 | 2/2011 | Sugaya |
| 2012/0232386 A1 | 9/2012 | Mansi et al. |

\* cited by examiner

DEVICE AND METHOD FOR THE COMPUTER-ASSISTED SIMULATION OF SURGICAL INTERVENTIONS

CROSS REFERENCE TO RELATED APPLICATIONS

This application claims priority to German Application No. 102015208804.9, having a filing date of May 12, 2015, the content of which is hereby incorporated by reference to the extent that it is not inconsistent with the present disclosure

FIELD OF TECHNOLOGY

The following relates to a device and method for a computer-assisted simulation of a surgical intervention.

BACKGROUND

In clinical practice, surgical interventions are generally planned on the basis of medical image recordings in combination with recommendations from clinical guidelines. However, a substantial portion of the planning and the success of an intervention can be apportioned to the experience of the performing surgeon or surgeons. Many interventions, such as e.g. heart valve repairs, especially require good planning, experience and surgical skill. It is therefore a goal worth striving for to assist the surgeon when planning and training interventions to the best possible extent.

The practice of using decision assistance systems for planning surgical interventions, which decision assistance systems are based on a simulation of physiological structures and functions, such as e.g. of a heart valve, by means of a biomechanical model, are known. By way of example, such biomechanical simulations of heart valves are known from documents U.S. 2010/0240996 A1 and U.S. 2012/0232386 A1. By way of such simulations, it is possible to estimate an effect of a surgical intervention and this can be used to plan the intervention. However, use of such simulation tools generally requires a complicated induction due to the complexity thereof Furthermore, the practice of recording a real surgical intervention by way of a camera fastened to the head of the surgeon and transmitting the resulting video stream to observers, who can therefore follow the intervention from the view of the performing surgeon, for the purposes of training in surgical interventions is known from, for example, the website http://www.surgevry.com by Surgevry. However, this only allows the observers to have passive training of the intervention.

SUMMARY

An aspect relates to a device and a method for the computer-assisted simulation of surgical interventions, which allow improved assistance of the surgeon.

In the device according to embodiments of the invention for the computer-assisted simulation of surgical interventions, provision is made for a first interface for reading image data of an anatomical region obtained by means of a medical imaging method. In this case, the image data can originate from e.g. sonographic, radiological, angiographic or tomographic image recordings. The anatomical region can be e.g. an organ, an organ region or a different tissue or body structure. A modeling module serves to establish a volumetric biomechanical structure model of the anatomical region on the basis of the image data. Moreover, provision is made for a tracking module, couplable with a camera, for video-based registration of spatial gestures of a user. Furthermore, a simulation module serves to assign a gesture registered in each case to a simulated mechanical effect on the anatomical region on the basis of the biomechanical structure model, to simulate a mechanical reaction of the anatomical region to the simulated mechanical effect on the basis of the biomechanical structure model, and to modify the biomechanical structure model in accordance with the simulated mechanical reaction. Moreover, provision is made for a visualization module for the volumetric visualization of the biomechanical structure model. The visualization module preferably visualizes, in particular, the mechanical reaction of the anatomical region and/or the modified biomechanical structure model.

The method steps to be carried out by the device described above are the subject matter of the method according to embodiments of the invention for computer-assisted simulation of surgical interventions.

A substantial advantage of embodiments of the invention can be viewed in the fact that a user, e.g. a surgeon, can simulate a surgical intervention in a comparatively realistic manner, both in respect of the manual performance thereof and also in respect of the visualization. In particular, he can undertake substantially the same manipulations on the biomechanical structure model as he can during a real intervention. In this manner, the surgeon can test various therapeutic options and thus establish an ideal procedure. Therefore, embodiments of the invention allows the support of the surgeon in an intuitive manner, both when planning and when training interventions.

Advantageous embodiments and developments of the invention are specified in the dependent claims.

According to an advantageous embodiment of the invention, the tracking module can be configured to register gestures of the user carried out with a surgical instrument, e.g. a scalpel. In particular, it is possible to register movements of one or more specific parts of the surgical instrument, for example of a blade and/or a handle of a scalpel. This is advantageous to the extent that the user can handle the surgical instrument within the scope of the simulation in the same way as during a real intervention.

Furthermore, provision can be made for a haptic interface for the haptic output of the simulated mechanical reaction to the user. This allows feedback, which is perceivable immediately and in a realistic manner by the user, about the simulated mechanical reaction of the anatomical region to the simulated mechanical effect.

According to an advantageous development of embodiments of the invention, the simulation module can be configured to simulate an effect of a surgical intervention on an anatomical function of the anatomical region on the basis of the biomechanical structure model. Here, provision can be made for an output interface for displaying the simulated effect. In this way it is possible to predict or at least estimate consequences of an intervention. As a result, the user can test various therapeutic options and establish a procedure that is ideal in respect to the consequences.

Advantageously, the biomechanical structure model can be patient specific. This allows patient-specific planning and patient-specific training of an intervention.

According to an advantageous embodiment, the biomechanical structure model can comprise a finite element model. It is possible to use a multiplicity of available, well-engineered software tools for the purposes of an efficient creation and calculation of such finite element models.

Moreover, the modeling module can be configured to dynamically adapt the biomechanical structure model on the basis of continuously read image data.

Furthermore, the first interface can be configured to read the image data in a time-resolved manner. Accordingly, the modeling module can be configured to identify movement dynamics of a substructure of the anatomical region on the basis of the time-resolved image data and to derive a physical property of the substructure on the basis of the identified movement dynamics and map this in the biomechanical structure model. In this way, it is possible to obtain a comparatively exact physical simulation of the anatomical region and the mechanical reactions thereof to the mechanical effects.

In particular, the modeling module can comprise a module for machine learning which is configured to identify the movement dynamics of the substructure, derive the physical property of the substructure and/or map the physical property in the biomechanical structure model. Such a module for machine learning can, for example, comprise an artificial neural network and/or a so-called probabilistic boosting tree.

Moreover, the visualization module can be designed as an immersive system for displaying virtual and/or augmented reality. Alternatively or additionally, the visualization module can also be designed as a holographic and/or stereographic visualization system. Such a visualization module increases the impression of reality of the user within the scope of the simulation.

BRIEF DESCRIPTION

Some of the embodiments will be described in detail, with reference to the following figures, wherein like designations denote like members, wherein.

DETAILED DESCRIPTION

Figure 1:
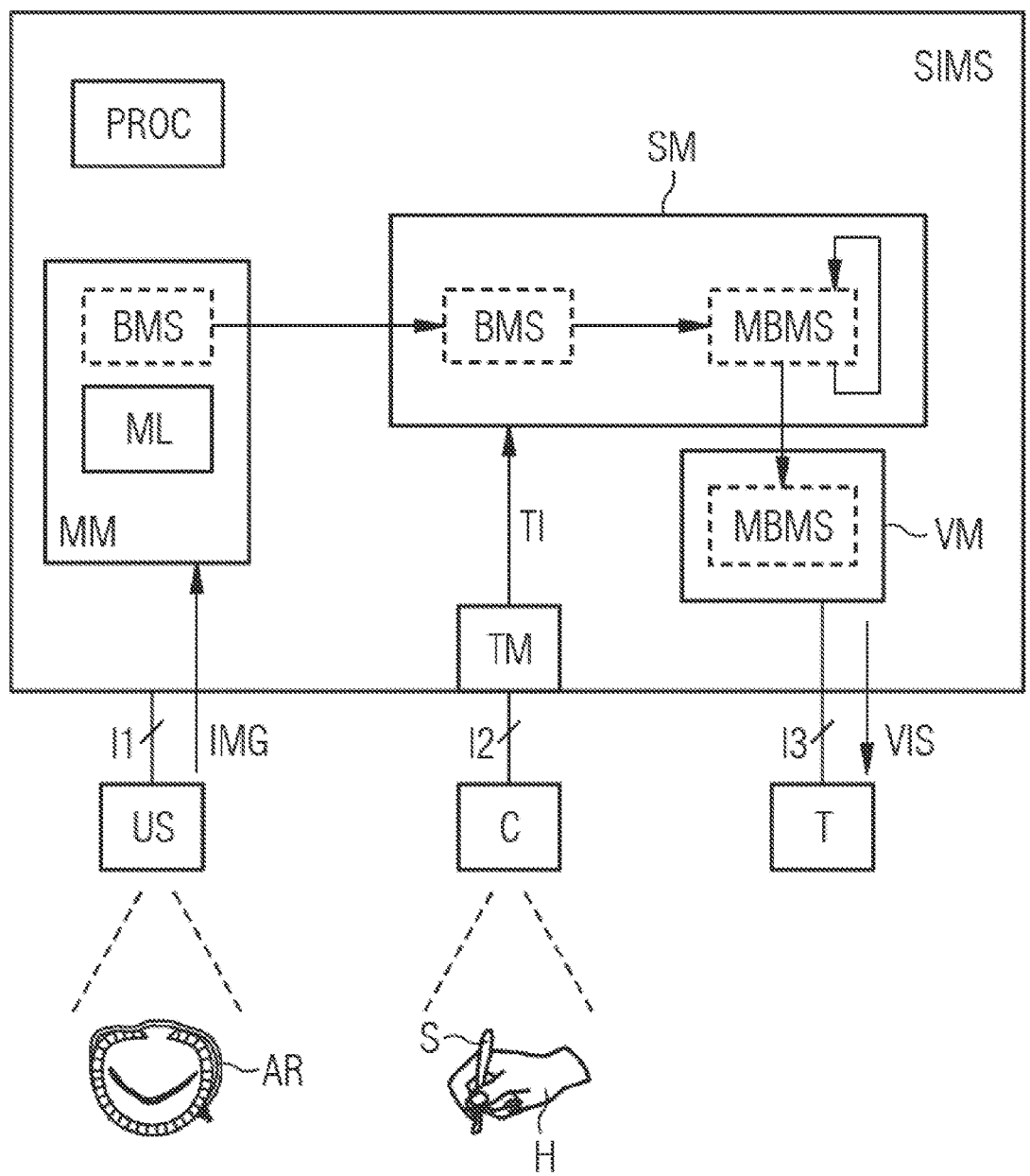
FIG. 1 shows a simulation device.

FIG. 1 schematically shows a simulation device SIMS according to embodiments of the invention for simulating surgical interventions. The simulation device SIMS comprises a processor PROC and/or one or more other computer apparatuses for executing the method according to embodiments of the invention. A medical image recording apparatus US is coupled to the simulation device SIMS by way of a first interface I1. By way of example, the image recording device US can be an ultrasonic recording apparatus, an x-ray tube, a magnetic resonance imaging scanner or any other medical recording device which supplies image recordings of anatomical regions, e.g. organs, organ regions or other body and/or tissue structures. The image recording apparatus US is configured to record time-resolved, preferably volumetric, image recordings of the respective anatomical region continuously and transfer these continuously as time-resolved, preferably volumetric, image data IMG to the simulation device SIMS by way of the first interface I1.

For the present exemplary embodiment, the assumption is made that a heart valve is recorded in the anatomical surroundings thereof and/or in the anatomical functional context thereof as an anatomical region AR by way of the image recording apparatus US. The image data IMG of the anatomical region AR, i.e. of the heart valve, are transferred, for example as a video data stream, from the image recording apparatus US to a modeling module MM of the simulation device SIMS.

The modeling module MM serves to establish a volumetric biomechanical structure model BMS of the anatomical region AR on the basis of the image data IMG. To the extent that the biomechanical structure model BMS is established on the basis of the image data IMG of the anatomical region AR of a patient, the biomechanical structure model BMS is patient specific. The biomechanical structure model BMS preferably comprises a finite element model.

In order to establish the biomechanical structure model BMS, the time-resolved image data IMG are analyzed by the modeling module MM. Here, one or more substructures of the anatomical region AR are identified, for example by means of known pattern recognition methods, and movement dynamics of these substructures are established. The biomechanical structure model BMS, or a possibly underlying finite element model, is modified on the basis of the identified movement dynamics, for example by means of a numerical optimization method, until it reproduces the identified movement dynamics. Alternatively or additionally, parameters of the biomechanical structure model BMS can be estimated from the identified movement dynamics on the basis of learning-based regression methods, wherein a numerical optimization method is used during a learning phase. Using this, physical properties of the substructures can be derived on the basis of the identified movement dynamics and said physical properties can be mapped in the biomechanical structure model BMS. Here, the movement dynamics can be established, in particular also by employing the Doppler Effect, e.g. by using a Doppler ultrasonic instrument, for example by virtue of a blood flow being measured in this way. By way of example, the elasticity, rigidity, density or other tissue parameters of the substructures can be established as physical properties thereof. Preferably, the biomechanical structure model BMS is continuously adapted dynamically by the modeling module MM on the basis of the read image data IMG.

In the present exemplary embodiment, the modeling model MM comprises a module for machine learning ML for identifying the movement dynamics of the substructures, for deriving the physical properties of the substructures and/or for mapping the physical properties in the biomechanical structure model BMS. Here, in particular, the machine learning can be based on a comparison of the identified substructures of the anatomical region AR with a multiplicity of known anatomical structures, the movement dynamics thereof and/or the physical properties thereof. To this end, the modeling module MM can be coupled to a database (not depicted here), in which the multiplicity of known structures are stored in addition to the movement dynamics thereof and known physical properties, and it can use said database during the learning phase. The physical properties stored in the database can be established approximately by means of an optimization method on the basis of the biomechanical structure model BMS.

A camera C is connected by way of a second interface I2 of the simulation device SIMS. The camera C serves for the video-based recording of spatial gestures of a user, e.g. of a surgeon. Preferably, movements of the hand H of the surgeon carried out with a surgical instrument, e.g. a scalpel S, in a predetermined or adjustable spatial region are recorded as gestures. A resultant video data stream is fed to a tracking module TM of the simulation device SIMS and evaluated thereby. The gestures carried out by the hand H and the scalpel S are identified and parameterized by the tracking module TM. In particular, the movements of the surgical instrument, i.e. of the scalpel S and/or of the functional units or parts thereof, such as of the blade and/or handle thereof, in this case, are registered and tracked. The registered gestures and movements of the surgical instrument S are represented by tracking information TI by way of the tracking module TM.

By way of example, the tracking information TI comprises location, orientation, movement, movement direction, velocity and/or rotation of the hand H and of the scalpel S, preferably in each case for a multiplicity of specific points of the scalpel S, e.g. for the blade and/or handle thereof, and for specific points of the hand H, for example for different fingers, phalanges, knuckle joints and/or fingertips.

The simulation device SIMS furthermore comprises a simulation module SM for simulating the anatomical region AR on the basis of the biomechanical structure model BMS. The latter is transferred from the modeling module MM to the simulation module SM. Furthermore, the tracking information TI is transferred from the tracking module TM to the simulation module SM. On the basis of the transferred tracking information TI, the simulation module SM assigns a respectively registered gesture or a respective movement of the hand H and/or of the scalpel S to a mechanical effect, simulated on the basis of the biomechanical structure model BMS, on the anatomical region AR. Thus, for example, a movement of the fingertip of the hand H in a specific direction can be assigned to a mechanical pressure effect on a specifically assigned location of the anatomical region AR. Accordingly, a registered movement of the blade of the scalpel S can be assigned to a simulated cut at a specific location of the anatomical region AR.

The simulation module SM simulates a mechanical reaction of the anatomical region AR to the simulated mechanical effect on the basis of the biomechanical structure model BMS. Here, in particular, occurring forces and deformations and reversible changes, e.g. elastic deformations, and irreversible changes, e.g. a tissue cut, a suture and/or an implant, are simulated dynamically. The biomechanical structure model is modified by the simulation module SM in accordance with the simulated mechanical reaction. By way of example, in the case of an irreversible virtual tissue cut, tissue parts separated from one another by the tissue cut are virtually separated from one another in the biomechanical structure model BMS such that the separated cut surfaces can no longer exert pulling forces on one another in the simulation and can only still exert friction-based shearing forces. The modified biomechanical structure model is denoted by MBMS in FIG. 1. The latter is continuously modified by the simulation module SM by the continuously registered gestures of the surgeon and the mechanical reactions of the anatomical region AR derived therefrom and it is updated to some extent according to a virtual course of an operation.

Moreover, the simulation module SM simulates one or more effects of a virtual surgical intervention on an anatomical function of the anatomical region AR on the basis of the modified biomechanical structure model MBMS. In this manner, a success or consequences of the intervention can be predicted or at least estimated. In particular, such a prediction can be carried out by comparing the modified biomechanical structure model MBMS with a multiplicity of known cases stored in a database. To this end, use can preferably be made of the module for machine learning ML or a further module for machine learning.

The simulation device SIMS furthermore comprises a visualization module VM for volumetric visualization of the biomechanical structure model BMS and/or the modified biomechanical structure model MBMS. For this purpose, the modified biomechanical structure model MBMS is at least partly transferred from the simulation module SM to the visualization module VM in the present exemplary embodiment. The latter calculates a volumetric visualization of the modified biomechanical structure model MBMS and outputs volumetric visualization data VIS to a screen terminal T. The screen terminal T is coupled to the simulation device SIMS by way of a third interface I3. In particular, the visualization module VM visualizes the mechanical reactions of the anatomical region AR to the simulated mechanical effects. In this manner, the user can immediately identify what simulated effects his gestures carried out in conjunction with the simulated surgical intervention have on the anatomical region AR.

Preferably, an immersive system for displaying virtual and/or augmented reality can be used as a screen terminal T. Alternatively or additionally, use can be made of a holographic and/or stereographic visualization system. Moreover, the third interface I3 can serve as an output interface for displaying the simulated effect of the virtual intervention on the screen terminal T.

Additionally, the simulation device SIMS can have a haptic interface (not depicted here) for haptic output of the simulated mechanical reaction to the user. By way of example, such a haptic output can be provided by means of a so-called robotic glove or active glove.

Figure 2:
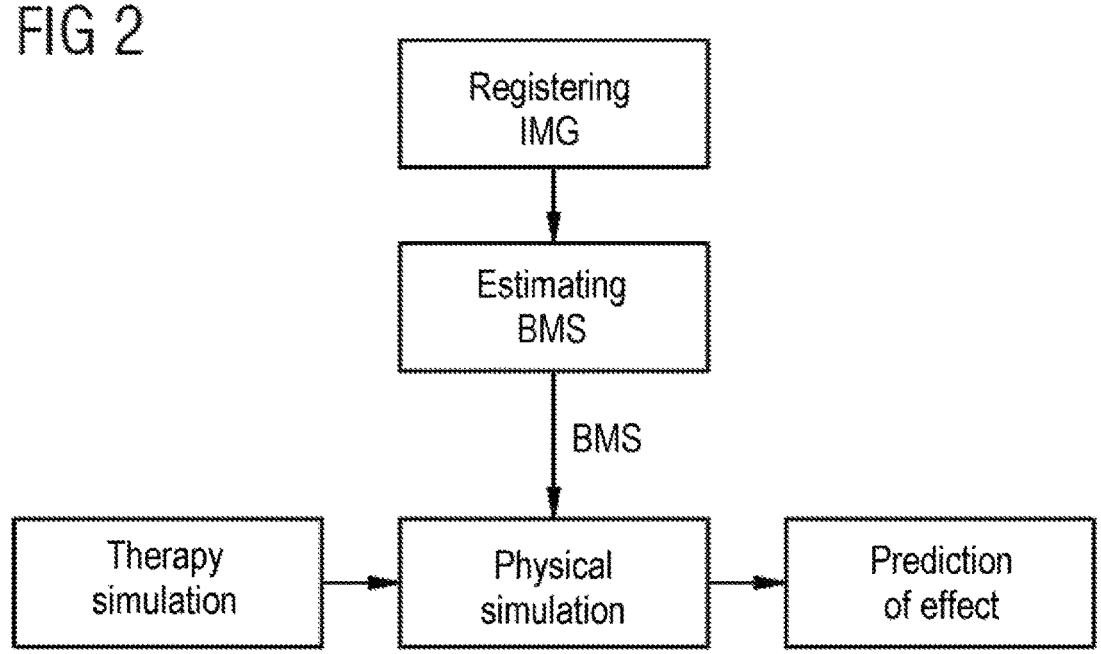
FIG. 2 shows a flowchart for elucidating processes of a method.

FIG. 2 shows a flowchart for elucidating processes of a method according to embodiments of the invention in a schematic illustration. Within the scope of the method according to embodiments of the invention, the image data IMG of the anatomical region AR are initially recorded and registered. The biomechanical structure model BMS is established on the basis of the registered image data IMG, for example by estimating. Then, a physical simulation of the anatomical region AR can be carried out by means of the biomechanical structure model BMS. A therapy simulation, e.g. by simulating a surgical intervention, can then resort to the physical simulation of the anatomical region AR in order to predict the effect of the therapy or the surgical intervention.

Figure 3:
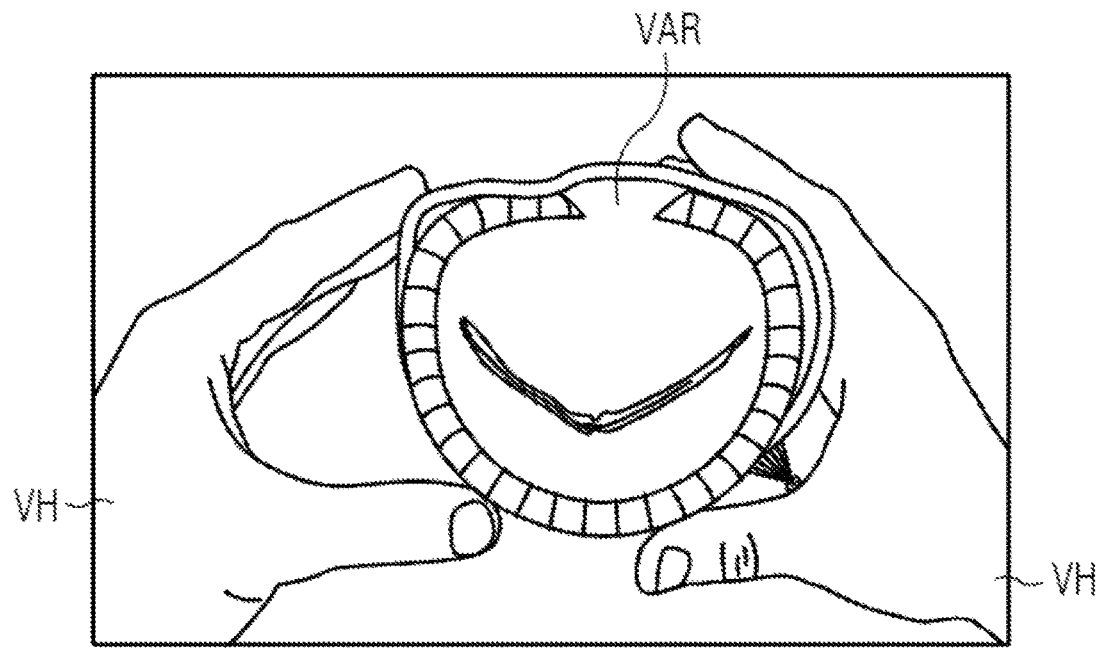
FIG. 3 shows a visualization of a virtual interaction with an anatomical region.

FIG. 3 elucidates a visualization of a virtual interaction of a user of the simulation device SIMS with an anatomical region AR. The visualization comprises a visualization VAR of the anatomical region AR and a visualization VH of hands or the gestures thereof registered by the tracking module TM. Here, registered positions and orientations of a multiplicity of phalanges are assigned to virtual positions and orientations of the visualization VH in the visualization VAR. The assignment of the positions and orientations of the phalanges to positions in the visualization VAR is carried out on the basis of the biomechanical structure model BMS of the anatomical region AR.

By means of embodiments of the invention, image data IMG, preferably obtained in vivo, e.g. by means of echocardiography, are used to generate a display of the anatomical region AR on the computer. A geometric configuration and other parameters of this display are preferably converted into a finite element model, by means of which a physiological and/or physical behavior of the anatomical region AR is simulated dynamically. Parameters of the biomechanical structure model BMS are established or estimated in a patient-specific manner on the basis of the movement dynamics or the movement flow in the anatomical region AR, which are derivable from the image data IMG.

During the planning phase for surgical intervention, the surgeon can test different procedures by means of the simulation device SIMS and simulate and estimate their respective effect on the anatomical function of the anatomical region AR. By the inclusion and the tracking of real surgical instruments handled in a natural manner and by using preferably immersive visualization techniques, a perceived realism of the simulation can be significantly increased. The use of such an immersive simulation system allows the surgeon to undertake the same manipulations virtually on the biomechanical structure model BMS as he would undertake in the case of an actual intervention. In this way, the surgeon can test and/or combine different therapeutic options in order thus to establish an ideal procedure before an actual intervention takes place. In addition to improved planning of surgical interventions, embodiments of the invention also allow improved training of surgeons.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A device for the computer-assisted simulation of surgical interventions, comprising
    a) a first interface for reading image data of an anatomical region obtained by means of a medical imaging method,
    b) a modeling module for establishing a volumetric biomechanical structure model of the anatomical region on the basis of the image data,
    c) a tracking module, couplable with a camera, for video-based registration of spatial gestures of a user,
    d) a simulation module
        for assigning a gesture registered in each case to a simulated mechanical effect on the anatomical region on the basis of the biomechanical structure model,
        for simulating a mechanical reaction of the anatomical region to the simulated mechanical effect on the basis of the biomechanical structure model, and
        for modifying the biomechanical structure model in accordance with the simulated mechanical reaction, and
    e) a visualization module for the volumetric visualization of the biomechanical structure model.

2. The device as claimed in claim 1, wherein the tracking module is configured to register gestures of the user carried out with a surgical instrument.

3. The device as claimed in claim 1, wherein by a haptic interface for the haptic output of the simulated mechanical reaction to the user.

4. The device as claimed in claim 1, wherein that the simulation module is configured to simulate an effect of the surgical intervention on an anatomical function of the anatomical region on the basis of the biomechanical structure model, and in that an output interface for displaying the simulated effect is provided.

5. The device as claimed in claim 1, wherein that the biomechanical structure model is patient specific.

6. The device as claimed in claim 1, wherein the biomechanical structure model comprises a finite element model.

7. The device as claimed in claim 1, wherein the modeling module is configured to dynamically adapt the biomechanical structure model on the basis of continuously read image data.

8. The device as claimed in claim 1, wherein that the first interface is configured to read the image data in a time-resolved manner and in that the modeling module is configured to identify movement dynamics of the substructure of the anatomical region) on the basis of the time-resolved image data and to derive a physical property of the substructure on the basis of the identified movement dynamics and map this in the biomechanical structure model.

9. The device as claimed in claim 8, wherein the modeling module comprises a module for machine learning which is configured to identify the movement dynamics of the substructure, derive the physical property of the substructure and/or map the physical property in the biomechanical structure model.

10. The device as claimed in claim 1, wherein the visualization module is designed as an immersive system for displaying virtual and/or augmented reality.

11. The device as claimed in claim 1, wherein the visualization module is designed as one of a holographic and stereographic visualization system.

12. A method for computer-assisted simulation of surgical interventions, wherein
    a) image data of an anatomical region obtained by means of a medical imaging method are read,
    b) a volumetric biomechanical structure model of the anatomical region is established on the basis of the image data,
    c) spatial gestures of a user are registered in a video-based manner,
    d) by way of a simulation module,
        a gesture registered in each case is assigned to a simulated mechanical effect on the anatomical region on the basis of the biomechanical structure model,
        a mechanical reaction of the anatomical region to the simulated mechanical effect is simulated on the basis of the biomechanical structure model, and
        the biomechanical structure model is modified in accordance with the simulated mechanical reaction, and
    e) the biomechanical structure model is visualized volumetrically.

13. A computer program product configured to implement a device as claimed in claim 1.

14. A computer program product configured to execute a method as claimed in claim 12.

* * * * *